United States Patent
Maeda et al.

(10) Patent No.: US 8,252,919 B2
(45) Date of Patent: Aug. 28, 2012

(54) 2'-HYDROXY-PROTECTED RIBONUCLEOSIDE DERIVATIVE AND PRODUCTION METHOD THEREOF

(75) Inventors: Hirofumi Maeda, Takasago (JP); Akio Fujii, Takasago (JP); Masaru Mitsuda, Takasago (JP)

(73) Assignee: Kaneka Corporation, Osaka (JP)

( * ) Notice: Subject to any disclaimer, the term of this patent is extended or adjusted under 35 U.S.C. 154(b) by 99 days.

(21) Appl. No.: 12/919,295

(22) PCT Filed: Feb. 26, 2009

(86) PCT No.: PCT/JP2009/053482
§ 371 (c)(1),
(2), (4) Date: Aug. 25, 2010

(87) PCT Pub. No.: WO2009/107692
PCT Pub. Date: Sep. 3, 2009

(65) Prior Publication Data
US 2011/0009609 A1  Jan. 13, 2011

(30) Foreign Application Priority Data
Feb. 29, 2008 (JP) .................... 2008-050658

(51) Int. Cl.
C07H 23/00 (2006.01)
C07H 19/00 (2006.01)
C07H 19/167 (2006.01)
C07H 19/173 (2006.01)

(52) U.S. Cl. .......... 536/26.5; 536/27.11; 536/27.23; 536/27.62; 536/27.81; 536/28.5; 536/28.53

(58) Field of Classification Search .............. None
See application file for complete search history.

(56) References Cited

U.S. PATENT DOCUMENTS 5,177,196 A  1/1993  Meyer, Jr. et al.
5,204,466 A  4/1993  Liotta et al.

FOREIGN PATENT DOCUMENTS

WO  92/03577  3/1992
WO  92/14743  9/1992

OTHER PUBLICATIONS

International Search Report issued Mar. 24, 2009 in International (PCT) Application No. PCT/JP2009/053482.
International Preliminary Report on Patentability together with English translation of Written Opinion issued Oct. 21, 2010 in International (PCT) Application No. PCT/JP2009/053482.
V. Serebryany et al., "An efficient preparation of protected ribonucleosides for phosphoramidite RNA synthesis", Tetrahedron Letters, vol. 43, 2002, pp. 1983-1985.
G.H. Hakimelahi, et al., "New catalysts and procedures for the dimethoxytritylation and selective silylation of ribonucleosides", Canadian Journal of Chemistry, vol. 60, 1982, pp. 1106-1113.
G.H. Hakimelahi, et al., "Nitrate Ion as Catalyst for Selective Silylations of Nucleosides", Tetrahedron Letters, vol. 22, No. 48, 1981, pp. 4775-4778.
I. Hirao et al., "Amines—phenyl isocyanate system for phenylcarbamoylation of the hydroxyl groups of ribonucleosides", Nucleic Acids Research Symposium Series, No. 10, 1981, pp. 33-36.
Y. Ishido et al., "Regioselective phenylcarbamoylation of hydroxy-groups of ribonucleosides with bis(tributyltin)oxide—phenyl isocyanate system," Nucleic Acids Research Symposium Series, No. 6, 1979, pp. 37-40.
Y. Ishido et al., "Regioselective Phenylcarbamoylation of the Hydroxyl Groups of Purine and Pyrimidine Ribonucleosides with Bis(Tributyltin) Oxide—Phenyl Isocyanate", Heterocycles, vol. 13, 1979, pp. 181-185.
W.L. Sung, "Synthesis of 4-(1,2,4-Triazol-1-yl)pyrimidin-2(1H)-one Ribonucleotide and Its Application in Synthesis of Oligoribonucleotides", Journal of Organic Chemistry, vol. 47, 1982, pp. 3623-3628.
M. Sukeda, et al., "The First Radical Method for the Introduction of an Ethynyl Group Using a Silicon Tether and Its Application to the Synthesis of 2'-Deoxy-2'-C-ethynylnucleosides", Journal of Organic Chemistry, vol. 68, 2003, pp. 3465-3475.
S. Couturier, et al., "Synthesis of 3'-deoxy-3'-C-methyl-β-D-ribonucleoside analogs", Tetrahedron, vol. 63, 2007, pp. 11260-11266.

*Primary Examiner* — Lawrence E Crane
(74) *Attorney, Agent, or Firm* — Wenderoth, Lind & Ponack, L.L.P.

(57) ABSTRACT

The present invention relates to a method for producing a 2'-hydroxy-protected nucleoside derivative by reacting a ribonucleoside with an acylating or a carbamoylating reagent in the presence of a metal complex consisting of a copper compound and an optically active ligand. By the method according to the present invention, a 2'-hydroxy-protected ribonucleoside derivative, which is an important intermediate for producing an oligonucleoside, can be easily produced with good regioselectivity from a nucleoside derivative of which 2',3'-hydroxy groups are not protected.

18 Claims, No Drawings

2'-HYDROXY-PROTECTED RIBONUCLEOSIDE DERIVATIVE AND PRODUCTION METHOD THEREOF

TECHNICAL FIELD

The present invention relate to a method for producing a 2'-hydroxy-protected ribonucleoside derivative. The 2'-hydroxy-protected ribonucleoside derivative is an important intermediate for producing an oligonucleoside.

BACKGROUND ART

In a general nucleotide unit for chemically synthesizing a RNA oligonucleotide, the 2'-hydroxy group is protected, 3'-hydroxy group is substituted by the group for elongating a phosphate bond and 5'-hydroxy group is protected. For example, in a phosphoramidite method, which is most commonly used at the present days among chemically synthesizing methods of oligonucleotide, a nucleotide which is protected at 2'-hydroxy group and 5'-hydroxy group by respectively different substituents and has a 2-cyanoethoxy-diisopropylphosphoramidite group at 3'-hydroxy group is used. It is needed for synthesizing such a nucleotide to discriminate the hydroxy groups at the 2'-, 3'- and 5'-positions, and introduce a protecting group or substituent suitable for each hydroxy groups.

The following method has been known as the method for introducing different substituents to 2'-hydroxy group and 3'-hydroxy group, both of which are secondary hydroxy groups.
(1) After 3'-hydroxy group and 5'-hydroxy group are protected with cross-linked silyl groups and the like, 2'-hydroxy group is protected with a suitable group. Next, the cross-linked silyl groups are removed, 5'-hydroxy group is protected, and then a substituent for elongating an intended phosphate bond is introduced to 3'-hydroxy group (Non-patent Document 1).

In addition, the following methods have been known as the method for directly protecting 2'-hydroxy group or 3'-hydroxy group of a nucleoside derivative of which 2',3'-hydroxy groups are not protected.
(2) Tert-butyldimethylsilylchloride is reacted in the presence of silver nitrate or a base (Non-patent Documents 2 and 3).
(3) Phenyl isocyanate is reacted in the presence of a base or a tin oxide (Non-patent Documents 4, 5 and 6).

Non-patent Document 1: TETRAHEDRON LETTERS, 2002, 43, 1983
Non-patent Document 2: CANADIAN JOURNAL OF CHEMISTRY, 1982, 1106
Non-patent Document 3: TETRAHEDRON LETTERS, 1981, 22, 4775
Non-patent Document 4: NUCLEIC ACIDS RESEARCH SYMPOSIUM SERIES, 1981, 10, 33
Non-patent Document 5: NUCLEIC ACIDS RESEARCH SYMPOSIUM SERIES, 1979, 6, S37
Non-patent Document 6: HETEROCYCLES, 1979, 13, 181

DISCLOSURE OF THE INVENTION

Problems to be Solved by the Invention

However, the method (1) requires a number of steps. In addition, an silyl group which is expensive and does not exist in the nucleotide as the target compound is required in the steps. The method (1) is therefore economically and industrially handicapped. In addition, the methods (2) and (3) is also economically and industrially handicapped, since the selectivity of 2'- and 3'-hydroxy groups is low in the reaction of the methods, and equivalent or more mole of silver nitrate, a base or a harmful tin compound to a nucleoside as the substrate should be used.

As mentioned above, conventional methods have a problem to be solved as industrial production methods.

Under the above-mentioned circumstance, the objective of the present invention is to provide a method for regioselectively introducing an intended protective group to 2'-hydroxy group, which method is effective and economical and can be preferably applied by industry.

Means for Solving the Problem

The present inventors studied very hard to achieve the above objective. As a result, the inventors found that an intended protective group can be introduced at the 2'-hydroxy group of a nucleoside with high regioselectivity by carrying out a reaction in the presence of a copper complex consisting of a copper compound and an optically active ligand, to complete the present invention.

The present invention relates to a method for producing a 2'-hydroxy-protected ribonucleoside derivative, characterized in:

that the 2'-hydroxy-protected ribonucleoside derivative is represented by the formula (2):

wherein, $R^1$ is a hydrogen atom or a protective group for a hydroxy group; $R^2$ is an acyl group; B is adenine, guanine, cytosine, uracil or a derivative group thereof, represented by the following formula:

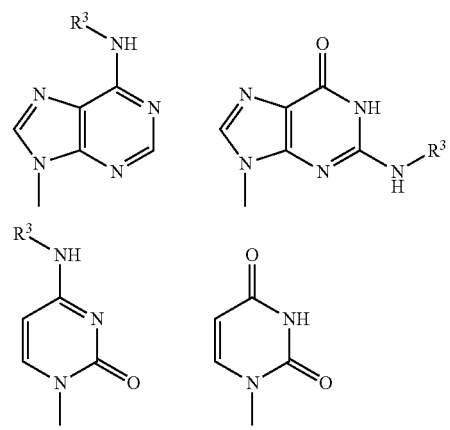

wherein, $R^3$ is a hydrogen atom or a protective group for an amino group;

and comprising a step of reacting a ribonucleoside represented by the formula (1):

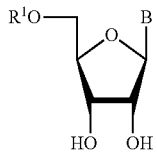
(1)

wherein, $R^1$ and B mean the same as the above,
with an acylating reagent in the presence of a copper complex consisting of a copper compound and an optically active ligand, to regioselectively introduce an acyl group to the 2'-hydroxy group.

In addition, the present invention relates to a 5'-O-[bis(4-methoxyphenyl)phenylmethyl]-2'-O-arylcarbamoyl nucleoside derivative, represented by the formula (5):

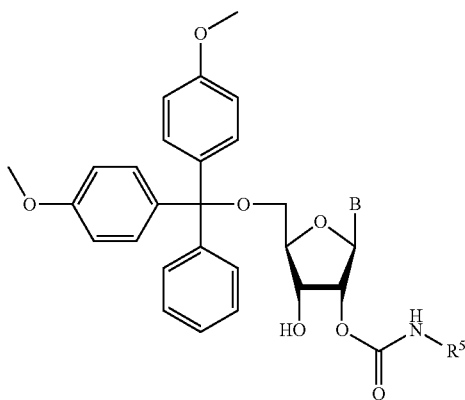
(5)

wherein, B means the same above; and $R^5$ is an optionally substituted aryl group having 6 to 18 carbon atoms.

Furthermore, the present invention relates to a 5'-O-[bis(4-methoxyphenyl)phenylmethyl]-2'-O-arylcarbamoyl ribonucleotide 3'-(2-cyanoethyl diisopropylphosphoramidite) derivative represented by the formula (6):

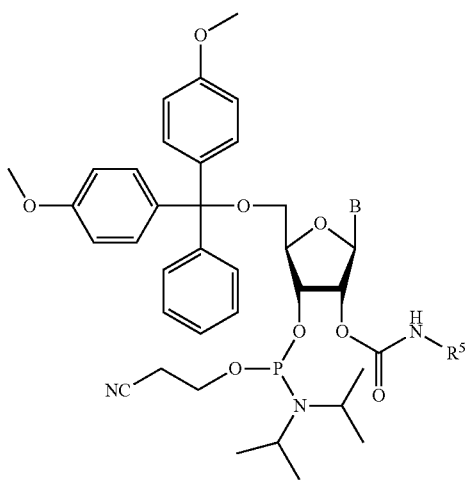
(6)

wherein, B and $R^5$ mean the same above.

The Effect of the Invention

By the production method according to the present invention, a 2'-protected nucleoside derivative can be easily produced with high regioselectivity from a nucleoside derivative of which 2'-, 3'-hydroxy groups are not protected.

MODE FOR CARRYING OUT THE INVENTION

Hereinafter, the present invention is explained in detail.

In the present invention, a ribonucleoside represented by the formula (1) (the compound is hereinafter called as "ribonucleoside (1)" in some cases):

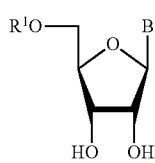
(1)

is reacted with an acylating reagent in the presence of a copper complex consisting of a copper compound and an optically active ligand. As a result, an acyl group is regioselectively introduced to the 2'-hydroxy group, to obtain a 2'-hydroxy-protected ribonucleoside derivative represented by the formula (2):

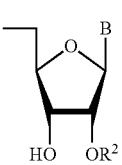
(2)

First, the compounds used for the reaction are explained as below.

As the nucleoside represented by the formula (1) in the present invention, adenosine, guanosine, cytidine, uridine and derivatives thereof are exemplified.

In the formula (1), $R^1$ is a hydrogen atom or a protective group for a hydroxy group. As the protective group for a hydroxy group, general protective groups for a hydroxy group, for example, trityl groups such as a 4,4'-dimethoxytrityl group and a 4-methoxytrityl group; and silyl groups such as a tert-butyldimethylsilyl group, a tert-butyldiphenylsilyl group and a triisopropylsilyl group, are exemplified.

The "B" is adenine, guanine, cytosine, uracil or the derivative thereof, represented by the following formula:

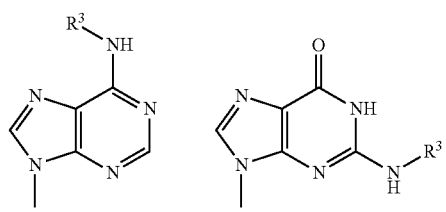

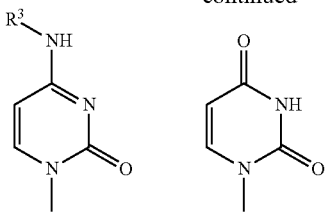

In the "B", $R^3$ on the amino group in adenine, guanine, cytosine is a hydrogen atom or protective group for an amino group. As a protective group for an amino group, a general protective group for an amino group is used. Such a protective group specifically includes acyl groups such as acetyl, benzoyl and phenoxyacetyl; alkyl groups such as benzyl and dimethoxytrityl; carbamate groups such as tert-butyl dicarbonate and benzyl carbamate; cyclic imide groups such as phthalimide; sulfonyl groups such as toluenesulfonyl; silyl groups such as tert-butyldimethylsilyl; imino groups such as N,N-dimethylaminomethyl and N,N-dibutylaminomethyl. Among the groups, an acyl group, an alkyl group and an imino group are preferable in terms of reactivity and economic efficiency.

An acylating reagent or carbamoylating reagent used in the present invention includes carboxylic acid halides such as acetyl chloride, benzoyl chloride and phenoxyacetyl chloride; carboxylic acid anhydrides such as acetic anhydride and benzoic anhydride; halogenated formic acid esters such as methyl chlorocarbonate and benzyloxycarbonyl chloride; pyrocarbonate diesters such as di-tert-butyl dicarbonate; isocyanic acid esters such as phenyl isocyanate and butyl isocyanate; isothiocyanic acid esters such as phenyl isothiocyanate and butyl isothiocyanate; and is preferably a carboxylic acid halide and an isocyanic acid ester, and is more preferably an isocyanic acid ester in terms of reactivity.

An isocyanic acid ester is not particularly limited; but a compound represented by the formula (4):

$$R^4NCO \quad (4)$$

is preferably used in terms of reactivity.

In the above formula (4), $R^4$ is an optionally substituted alkyl group having 1 to 18 carbon atoms, an optionally substituted cycloalkyl group having 1 to 18 carbon atoms, an optionally substituted aryl group having 6 to 18 carbon atoms, an optionally substituted aralkyl group having 7 to 18 carbon atoms, an optionally substituted sulfonyl group or an optionally substituted silyl group.

As the specific $R^4$, alkyl groups such as methyl, ethyl, propyl, isopropyl, butyl, isobutyl, tert-butyl, pentyl, isopentyl, hexyl, isohexyl, heptyl, isoheptyl, octyl and isooctyl; cycloalkyls such as cyclopropyl, cyclobutyl, cyclopentyl and cyclohexyl; aralkyl groups such as benzyl, 1-phenylethyl, 2-phenylethyl, 1-methylnaphthyl, 2-methylnaphthyl, 1-ethylnaphthyl and 2-ethylnaphthyl; aryl groups such as phenyl, 1-naphthyl, 2-naphthyl, 1-anthryl, 2-anthryl, 9-anthryl, 1-phenanthryl, 9-phenanthryl and 10-phenanthryl; sulfonyl groups such as methanesulfonyl, ethanesulfonyl, benzenesulfonyl and toluenesulfonyl; silyl groups such as trimethylsilyl, triethylsilyl, triphenylsilyl, tert-butyldimethylsilyl, tert-butyldiphenylsilyl, dimethylphenylsilyl, dimethylbenzylsilyl, diphenylmethylsilyl are exemplified. Among them, an alkyl group and an aryl group are preferable, an aryl group is more preferable, and a phenyl group is especially preferable in terms of regioselectivity.

The groups may have a substituent. Such a substituent includes halogen atoms such as a fluorine atom, a chloride atom, a bromine atom and iodine atom; alkyl groups such as methyl, ethyl, propyl, isopropyl, butyl, isobutyl, tert-butyl, pentyl, isopentyl, hexyl, isohexyl, heptyl, isoheptyl, octyl and isooctyl; cycloalkyl groups such as cyclopropyl, cyclobutyl, cyclopentyl, cyclohexyl; aralkyl groups such as benzyl, 1-phenylethyl, 2-phenylethyl, 1-methylnaphthyl, 2-methylnaphthyl, 1-ethylnaphthyl, 2-ethylnaphthyl; aryl groups such as phenyl, 1-naphthyl, 2-naphthyl, 1-anthryl, 2-anthryl, 9-anthryl, 1-phenanthryl; alkoxy groups such as methyloxy, ethyloxy, propyloxy, t-butyloxy, pentyloxy, isopentyloxy, hexyloxy, heptyloxy, octyloxy, cyclopropyloxy, cyclobutyloxy, 2-methylcyclopropyloxy, cyclopropylmethyloxy, cyclopentyloxy, cyclohexyloxy; amino group; mono- or dialkylamino groups such as N-methylamino, N-cyclohexylamino, N,N-dimethylamino, N,N-diethylamino, N,N-diisopropylamino; mono- or diarylamino groups such as N-phenylamino, N-naphthylamino, N,N-diphenylamino, N-naphthyl-N-phenylamino; mono- or diaralkyl groups such as N-benzylamino, N,N-dibenzylamino; nitro group. The number of the substituent may be one or not less than 2, and the position of the substituent is not particularly limited.

In the above formula (2), $R^2$ is the acyl group introduced by the reaction with an acylating group, and specifically includes esters such as acetate, benzoate and phenoxyacetate; carbonate; carbamate; and thiocarbamate. Among them, carbamate is preferable in terms of reactivity.

In the reaction, a metal complex consisting of a copper compound and an optically active ligand is used. As a result, it becomes possible to introduce a protective group to the 2'-hydroxy group with high selectivity. In particular, regioselectivity can be further improved by appropriately selecting the ligand depending the structure of a substrate.

As the copper compound, the compound represented by the formula (3):

$$CuX_2 \quad (3)$$

is used.

In the above formula (3), X is a halogen atom, OTf, $ClO_4$, $BF_4$, $SbF_6$ or $PF_6$. Among them, X is preferably a halogen atom or OTf in terms of reactivity and regioselectivity, and is more preferably Cl or OTf.

The copper compound specifically includes copper (II) chloride, copper (I) chloride, copper (II) trifluoromethanesulfonate, copper (II) sulfate, copper perchlorate (II), copper (II) nitrate, copper (I) bromide, copper (II) bromide, copper (I) iodide, copper (II) acetate, copper (II) acetylacetonate, copper (II) benzoate, copper (II) benzoylacetonate, copper (II) carbonate, copper (I) cyanide, copper (II) ammonium chloride, copper (II) ethylacetoacetate, copper (II) formate, copper (II) tetrafluoroborate, copper (II) hexafluoroantimonate and copper (II) hexafluorophosphate. Among them, copper (II) chloride and copper (II) trifluoromethanesulfonate are preferable in terms of reactivity and regioselectivity. One copper compound may be solely used and two or more may be used in combination.

The optically active ligand is not limited as long as the ligand has not less than 1 of asymmetric source in the molecule; and specifically includes optically active phosphoric ligands such as 2,2'-bis-(diphenylphosphino)-1,1'-binaphthyl, and optically active imine ligands. is preferably. Among them, an optically active nitrogen-containing ligand is preferable, and an optically active imine ligand is more preferable.

As the optically active imine ligand, the compounds represented by the formula (10):

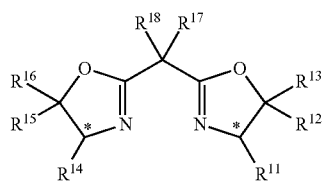

(10)

or represented by the formula (11):

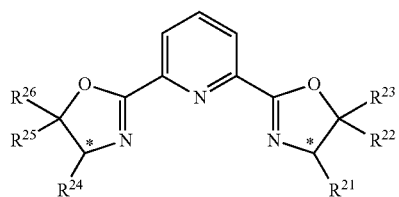

(11)

are preferably used.

In the formula (10), $R^{11}$ and $R^{14}$ are independently an optionally substituted alkyl group, an optionally substituted alkenyl group, an optionally substituted alkynyl group, an optionally substituted cycloalkyl group, an optionally substituted aralkyl group or an optionally substituted aryl group.

The $R^{12}$, $R^{13}$, $R^{15}$ and $R^{16}$ are independently a hydrogen atom, an optionally substituted alkyl group, an optionally substituted alkenyl group, an optionally substituted alkynyl group, an optionally substituted cycloalkyl group, an optionally substituted aralkyl group or an optionally substituted aryl group.

The $R^{11}$ may be bound to $R^{12}$ or $R^{13}$ and $R^{14}$ may be bound to $R^{15}$ or $R^{16}$, to form a ring.

The $R^{17}$ and $R^{18}$ may be the same or different each other, and are a hydrogen atom, an alkyl group or a cycloalkyl group.

The "*" indicates an asymmetric carbon.

The alkyl group of $R^{11}$, $R^{12}$, $R^{13}$, $R^{14}$, $R^{15}$ and $R^{16}$ in the formula (10) includes, for example, methyl, ethyl, propyl, isopropyl, butyl, isobutyl, tert-butyl, pentyl, isopentyl, hexyl, isohexyl, heptyl, isoheptyl, octyl and isooctyl.

The alkenyl group includes, for example, ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl.

The alkynyl group includes, for example, ethinyl, 1-propinyl, 2-propinyl, 1-butinyl, 2-butinyl, 3-butinyl, 1-pentinyl, 2-pentinyl, 3-pentinyl, 4-pentinyl and 1-hexiny.

The cycloalkyl group includes, for example, cyclopropyl, cyclobutyl, cyclopentyl and cyclohexyl.

The aralkyl group includes, for example, benzyl, 1-phenylethyl, 2-phenylethyl, 1-methylnaphthyl, 2-methylnaphthyl, 1-ethylnaphthyl and 2-ethylnaphthyl.

The aryl group includes, for example, phenyl, 1-naphthyl, 2-naphthyl, 1-anthryl, 2-anthryl, 9-anthryl and 1-phenanthryl.

The $R^{11}$, $R^{12}$, $R^{13}$, $R^{14}$, $R^{15}$ and $R^{16}$ may have a substituent on the appropriate carbon atom. Such a substituent specifically includes halogen atoms such as a fluorine atom, a chloride atom, a bromine atom and iodine atom; alkyl groups such as methyl, ethyl, propyl, isopropyl, butyl, isobutyl, tert-butyl, pentyl, isopentyl, hexyl, isohexyl, heptyl, isoheptyl, octyl and isooctyl; cycloalkyl groups such as cyclopropyl, cyclobutyl, cyclopentyl and cyclohexyl; aralkyl groups such as benzyl, 1-phenylethyl, 2-phenylethyl, 1-methylnaphthyl, 2-methylnaphthyl, 1-ethylnaphthyl and 2-ethylnaphthyl; aryl groups such as phenyl, 1-naphthyl, 2-naphthyl, 1-anthryl, 2-anthryl, 9-anthryl and 1-phenanthryl; alkoxy groups such as methyloxy, ethyloxy, propyloxy, t-butyloxy, pentyloxy, isopentyloxy, hexyloxy, heptyloxy, octyloxy, cyclopropyloxy, cyclobutyloxy, 2-methylcyclopropyloxy, cyclopropylmethyloxy, cyclopentyloxy and cyclohexyloxy; amino group; mono- or dialkylamino groups such as N-methylamino, N-cyclohexylamino, N,N-dimethylamino, N,N-diethylamino and N,N-diisopropylamino; mono- or diarylamino groups such as N-phenylamino, N-naphthylamino, N,N-diphenylamino and N-naphthyl-N-phenylamino; mono- or diaralkyl groups such as N-benzylamino and N,N-dibenzylamino; nitro group. The number of the substituent may be one or not less than 2, and the position of the substituent is not particularly limited.

The alkyl group of $R^{17}$ and $R^{18}$ can be specifically exemplified by methyl, ethyl, propyl, isopropyl, butyl, isobutyl, tert-butyl, pentyl, isopentyl, hexyl, isohexyl, heptyl, isoheptyl, octyl and isooctyl. The cycloalkyl group can be specifically exemplified by cyclopropyl, cyclobutyl, cyclopentyl and cyclohexyl.

In the formula (11), $R^{21}$ and $R^{24}$ are independently an optionally substituted alkyl group, an optionally substituted alkenyl group, an optionally substituted alkynyl group, an optionally substituted cycloalkyl group, an optionally substituted aralkyl group or an optionally substituted aryl group.

The $R^{22}$, $R^{23}$, $R^{25}$ and $R^{26}$ are independently a hydrogen atom, an optionally substituted alkyl group, an optionally substituted alkenyl group, an optionally substituted alkynyl group, an optionally substituted cycloalkyl group, an optionally substituted aralkyl group or an optionally substituted aryl group.

The $R^{21}$ may be bound to $R^{22}$ or $R^{23}$ and $R^{24}$ may be bound to $R^{25}$ or $R^{26}$, to form a ring.

The "*" indicates an asymmetric carbon.

In the formula (11), the specific example of the alkyl group, alkenyl group, alkynyl group, cycloalkyl group, aralkyl group and aryl group includes those for $R^{11}$ to $R^{16}$.

The $R^{22}$, $R^{23}$, $R^{25}$ and $R^{26}$ are preferably hydrogen atoms. The $R^{21}$ and $R^{24}$ are preferably isopropyl groups in terms of reactivity and regioselectivity.

The $R^{21}$, $R^{22}$, $R^{23}$, $R^{24}$, $R^{25}$ and $R^{26}$ may have a substituent on the appropriate carbon atom, and the same substituent of the formula (10) can be exemplified as such a substituent.

As the optically active imine ligand specifically includes 2,2'-isopropylidenebis[(4R)-4-phenyl-2-oxazoline], 2,2'-isopropylidenebis[(4R)-4-methyl-2-oxazoline], 2,2'-isopropylidenebis[(4R)-4-isopropyl-2-oxazoline], 2,2'-isopropylidenebis[(4R)-4-tert-butyl-2-oxazoline], 2,2'-isopropylidenebis[(4R)-4-benzyl-2-oxazoline], 2,2'-isopropylidenebis[(4S)-4-phenyl-2-oxazoline], 2,2'-isopropylidenebis[(4S)-4-methyl-2-oxazoline], 2,2'-isopropylidenebis[(4S)-4-isopropyl-2-oxazoline], 2,2'-isopropylidenebis[(4S)-4-tert-butyl-2-oxazoline], 2,2'-isopropylidenebis[(4S)-4-benzyl-2-oxazoline], 2,2'-bis[(4R)-4-benzyl-2-oxazoline], 2,2'-bis[(4S)-4-benzyl-2-oxazoline], 2,2'-methylenebis[(4R)-4-phenyl-2-oxazoline], 2,2'-methylenebis[(4R)-4-methyl-2-oxazoline], 2,2'-methylenebis[(4R)-4-isopropyl-2-oxazoline], 2,2'-methylenebis[(4R)-4-tert-butyl-2-oxazoline], 2,2'-methylenebis[(4R)-4-benzyl-2-oxazoline], 2,2'-methylenebis[(4S)-4-phenyl-2- oxazoline], 2,2'-methylenebis[(4S)-4-methyl-2-oxazoline], 2,2'-methylenebis[(4S)-4-isopropyl-2-oxazoline], 2,2'-methylenebis[(4S)-4-tert-butyl-2-oxazoline], 2,2'-methylenebis[(4S)-4-benzyl-2-oxazoline], [3aS-[2(3'aR,8'aS),3'aα,8'aα]]-2,2'-methylenebis[3a,8a-dihydro-8H-indeno-[1,2-d]oxazole], 3aR-[2(3'aR,8'aS),3'aβ,8'aβ]]-2,2'-methylenebis[3a,8a-dihydro-8H-indeno-[1,2-d]oxazole], 2,6-bis[(4R)-isopropyl-2-oxazoline-2-yl]pyridine, 2,6-bis[(4R)-phenyl-2-oxazoline-2-yl]pyridine, 2,6-bis[(4R,5R)-4-methyl-5-phenyl-2-oxazolinyl]pyridine, 2,6-bis[(4S)-isopropyl-2-oxazoline-2-yl]pyridine, 2,6-bis[(4S)-phenyl-2-oxazoline-2-yl]pyridine, 2,6-bis[(4S,5S)-4-methyl-5-phenyl-2-oxazolinyl]pyridine.

The ligand is preferably 2,2'-isopropylidenebis[(4S)-4-phenyl-2-oxazoline], 2,2'-isopropylidenebis[(4S)-4-isopropyl-2-oxazoline], 2,2'-isopropylidenebis[(4S)-4-tert-butyl-2-oxazoline], 2,2'-isopropylidenebis[(4S)-4-benzyl-2-oxazoline], 2,6-bis[(4S)-isopropyl-2-oxazoline-2-yl]pyridine, 2,2'-methylenebis[(4S)-4-benzyl-2-oxazoline] or 3aR-[2(3'aR,8'aS),3'aβ,8'aβ]]-2,2'-methylenebis[3a,8a-dihydro-8H-indeno-[1,2-d]oxazole], and is more preferably 2,6-bis[(4S)-isopropyl-2-oxazoline-2-yl]pyridine in terms of reactivity and regioselectivity.

The reaction may be carried out in the presence of a base.

The base specifically includes amine compounds such as triethylamine, tripropylamine, tributylamine, diisopropylethylamine, N,N,N',N'-tetramethylethylenediamine, dibenzylmethylamine, benzyldimethylamine, diphenylbenzylamine, pyridine, 4-N,N-dimethylaminopyridine, N-methylpyrrole, N-methylimidazole and diphenylmethylamine; inorganic carbonates such as sodium carbonate, magnesium carbonate, calcium carbonate, lithium carbonate, potassium carbonate, sodium hydrogencarbonate and lithium hydrogencarbonate; hydroxides such as sodium hydroxide, potassium hydroxide, lithium hydroxide, potassium hydroxide and magnesium hydroxide; alkali metal alkoxides such as sodium methoxide, sodium ethoxide and potassium-tert-butoxide; alkali metal hydrides such as sodium hydride and potassium hydride. The base is preferably triethylamine, diisopropylethylamine and potassium carbonate in terms of reactivity and regioselectivity.

In general, a reaction solvent is used in the reaction. The reaction solvent is not particularly limited as long as the solvent does not inhibit the reaction, and includes, for example, hydrocarbon solvents such as pentane, hexane, heptane, cyclohexane, petroleum ether; ester solvents such as ethyl acetate and methyl acetate; aromatic hydrocarbon solvents such as toluene, benzene and xylene; nitrile solvents such as acetonitrile and propionitrile; ether solvents such as tert-butylmethylether, diethylether, dimethylether, diisopropylether, tetrahydrofuran and dioxiane; amide solvents such as N,N-dimethylformamide and N,N-dimethylacetoamide; sulfoxide solvents such as dimethylsulfoxide; halogenated hydrocarbon solvents such as methylene chloride, 1,2-dichloroethylene, chloroform and carbon tetrachloride; carboxylic acid solvents such as acetic acid and formic acid. The solvent is preferably tetrahydrofuran or dioxiane in terms of reactivity and regioselectivity. Two or more solvents may be mixed. When such a mixed solvent is used, the mixture ratio is not especially limited.

Next, the reaction is explained in detail.

In the reaction, ribonucleoside (1) is reacted with an acylating reagent in the presence of a metal complex.

The acylating reagent may be used at the ratio of 0.5 to 10 molar, preferably 0.8 to 3 molar, more preferably 0.8 to 1.5 molar, relative to 1 molar of the ribonucleoside (1).

The copper compound constituting the metal complex may be used at the ratio of 0.00001 to 1 molar, preferably 0.005 to 0.5 molar, and more preferably 0.001 to 0.2 molar in terms of economic efficiency, relative to 1 molar of the ribonucleoside (1).

The ligand constituting the metal complex may be used at the ratio of 0.00001 to 1 molar, preferably 0.005 to 0.5 molar, and more preferably 0.001 to 0.2 molar in terms of economic efficiency, relative to 1 molar of the ribonucleoside (1). In particular, when an optically active imine ligand is used as the ligand, the ligand may be used at the ratio of 0.00001 to 1 molar, preferably 0.005 to 0.5 molar, and more preferably 0.001 to 0.2 molar in terms of economic efficiency, relative to 1 molar of the ribonucleoside (1).

The metal complex can be produced in the reaction from the copper compound and optically active ligand, or produced by reacting the copper compound with the optically active ligand and purifying from the mixture to be used.

When a base is used in the present invention, the amount of the base is not limited. The amount is generally 0.0001 to 10 molar, preferably 0.0005 to 5 molar, more preferably 0.001 to 1 molar, relative to 1 molar of the ribonucleoside (1).

The mixing order of each compound when the reaction carried out is not limited; however, in general, the ribonucleoside (1) and acylating reagent may be sequentially added to the solution of the metal complex. When a base is used, the base may be added before or after the addition of the ribonucleoside (1) and acylating reagent.

The concentration of the compounds when the reaction carried out varies with the kind of the used solvent; however, the concentration is generally 0.1 to 30 wt %, preferably 0.5 to 20 wt % in terms of regioselectivity and economic efficiency, and more preferably 1 to 20 wt %, since regioselectivity is lowered when the concentration is too high.

The temperature during the reaction varies with the kind of the used compound, copper complex, optically active ligand and base; however, the temperature is generally within the range of the solidification point to boiling point of the used reaction solvent. It is better to carry out the reaction at high temperature to complete the reaction in a short time, and it is better to carry out the reaction at lower temperature to inhibit side reaction. When the reaction is carried out at high temperature, there is fear that regioselectivity is lowered. The temperature is therefore preferably −78 to 100° C., more preferably −40 to 30° C. in terms of regioselectivity, and further preferably −30 to 30° C.

The reaction time varies with the kind of the used compound, copper complex, optically active ligand and base; in general, the time is preferably 0.1 to 96 hours when the reaction is carried out at the temperature of −40 to 30° C.

The reaction can be carried out in each conditions of normal pressure, reduced pressure and increased pressure. In addition, the reaction can be carried out in air and under an inert gas atmosphere, such as nitrogen, helium and argon.

After the reaction, a general post-processing for obtaining the product from a reaction mixture may be carried out. For example, water, hydrochloric acid, alkaline water or the like is added to the reaction mixture after the reaction, and then, extraction operation may be carried out using a general extraction solvent such as ethyl acetate, diethylether, methylene chloride and toluene. The target compound can be obtained by removing the reaction solvent and extraction solvent from the obtained extract under reduced pressure. Thus obtained product may be further purified by general purification methods such as silica gel column chromatography and recrystallization, if necessary.

It is possible to introduce a substituent for elongating a phosphate bond at the 3'-hydroxy group of the compound which can be obtained as the above and is represented by the formula (2) by phosphitylating and the like. As the compound into which the substituent for elongating a phosphate bond is introduced, phosphoric monoester, phosphoric diester, phosphorochloridite, phosphoramidite, phosphonate and the like can be exemplified.

As the compound represented by the formula (2), a 5'-O-[bis(4-methoxyphenyl)phenylmethyl]-2'-O-arylcarbamoyl-nucleoside derivative represented by the formula (5):

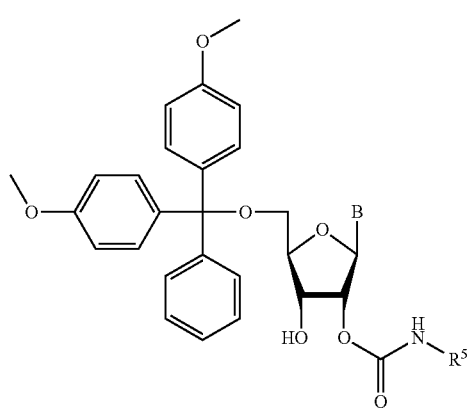

(5)

can be exemplified.

The above compound represented by the formula (5) can be phosphitylated by general condition such as the reaction with 2-cyanoethyl N,N-diisopropylchlorophosphoramidite in the presence of a base and the reaction with 2-cyanoethyl N,N,N',N'-tetraisopropylphosphoramidite in the presence of pyridine trifluoroacetate salt, to obtain 5'-O-[bis(4-methoxyphenyl)phenylmethyl]-2'-O-arylcarbamoylribonucleotide 3'-(2-cyanoethyl diisopropylphosphoramidite) derivative represented by the formula (6):

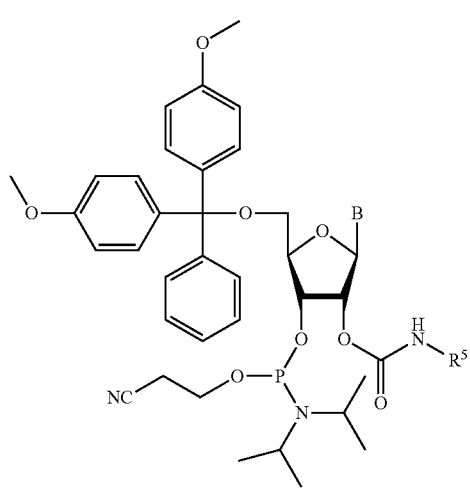

(6)

In the formulae (5) and (6), B means the same above.

The $R^5$ is an optionally substituted aryl group having 6 to 18 carbon atoms, such as phenyl, 1-naphthyl, 2-naphthyl, 1-anthryl, 2-anthryl, 9-anthryl and 1-phenanthryl. Among the groups, phenyl is preferable.

The compound represented by the formula (2) of which 3'-hydroxy group is phosphitylated and B is a cytosine derivative can be also obtained by derivatization from a uracil derivative.

As the derivatization method, a method for aminating the 4'-oxo group of the base part, i.e. uracil, can be applied. As the amination method, a method for directly substituting an oxo group with an amino group, a method for making an oxo group into an elimination group and changing the elimination group into an amino group (The Journal of Organic Chemistry, 2003, 68, 3465.), a method for making an oxo group into an azole group and changing the azole group into an amino group (The Journal of Organic Chemistry, 1982, 47, 3623.), and a method for making an oxo group into an thione group and changing the thione group into an amino group (Tetrahedron, 2007, 63, 11260.) can be exemplified. Hereinafter, the methods are explained in detail.

As a method for directly substituting an oxo group with an amino group, a method in which the compound (2) is reacted with ammonia gas, ammonia water, diazomethane and the like can be exemplified.

As a method for making an oxo group into an elimination group, a method in which an eliminable group is introduced in the presence of a base can be exemplified. Such an eliminable group includes silyl groups such as triphenylsilyl and triisopropylsilyl; sulfonyl groups such as 2,4,6-trimethylphenylsulfonyl, 2,4,6-triisopropylphenylsulfonyl, p-toluenesulfonyl and trifluoromethanesulfonyl; acyl groups such as trifluoroacetyl; phosphoryl groups such as dichlorophosphoryl.

The base used for the above methods specifically includes amine compounds such as triethylamine, tributylamine, 4-N,N-dimethylaminopyridine, N-methylimidazole, hexamethyldisilazane and pyridine; inorganic carbonates such as sodium carbonate, magnesium carbonate, calcium carbonate, lithium carbonate, potassium carbonate, sodium hydrogencarbonate, potassium hydrogencarbonate and lithium hydrogencarbonate; quaternary ammonium salts such as tetrabutylammonium bromide.

As a method for making an oxo group into an azole group, a method in which an intended azole compound is reacted in the presence of a base with a phosphorous compound or a sulfur compound can be exemplified. The azole group means a heterocyclic ring containing one or more nitrogen atoms.

As the azole compound, tetrazole, N-benzoyltetrazole, N-methylimidazole, imidazole, triazole, nitrotriazole and the like can be specifically exemplified. As the phosphorous compound, $POCl_2$, phosphorous trichloride, p-chlorophenyldichlorophosphineoxide and the like can be exemplified. As the sulfur compound, $SOCl_2$ and the like can be exemplified.

As the base, amine compounds such as triethylamine, tributylamine, 4-N,N-dimethylaminopyridine, N-methylimidazole, hexamethyldisilazane and pyridine; inorganic carbonates such as sodium carbonate, magnesium carbonate, calcium carbonate, lithium carbonate, potassium carbonate, sodium hydrogencarbonate, potassium hydrogencarbonate and lithium hydrogencarbonate; quaternary ammonium salts such as tetrabutylammonium bromide; and the like can be specifically exemplified.

As the method for replacing an oxo group by a thion compound, a method in which Lawesson's reagent, $P_4S_{10}$ or the like is used can be exemplified.

As the method for replacing an oxo group by an elimination group, azole group or thion and then transforming the group into amine, a method in which ammonias such as ammonia gas and aqueous ammonia; azide compounds such as sodium azide; alkylamine compounds such as methylamine and benzylamine; or arylamine compounds such as aniline is reacted can be exemplified.

The amino group at 4-position of the base obtained as the above is protected as necessary.

As the protective group, a general protective group for an amino group is used, and the protective group for the amino group of $R^3$ can be specifically exemplified. Among the groups, an acyl group, an alkyl group and an imino group are preferable in terms of reactivity and economic efficiency.

In the reactions, a reaction solvent is generally used. The reaction solvent is not limited as long as the solvent does not inhibit the reaction. As the solvent, the same solvent as exemplified for the reaction of ribonucleoside (1) with an acylating reagent can be used. In addition, reaction conditions such as reaction temperature and reaction time can be similar to ones for the reaction.

EXAMPLES

The present invention is described in more detail by the following examples; however, the present invention is by no means limited to the examples. The apparatus used for measuring the properties in the examples are shown as follows.

NMR: NMR A-400 manufactured by JEOL Ltd.

High-performance liquid chromatography: SPD-10Avp, LC-10ADvp, SCL-10Avp, DGU-12A, CTO-10ASvp, C-R8A, manufactured by shimadzu corporation Example 1

Production of 5'-O-[bis(4-methoxyphenyl)phenylmethyl]-2'-O-phenylcarbamoyl-uridine The THF solution (2 ml) including 2,6-bis[(4S)-isopropyl-2-oxazoline-2-yl]pyridine (0.05 mmol, 15.2 mg) and copper chloride (II) (0.05 mmol, 6.9 mg) was stirred for a day at room temperature. After the reaction mixture was cooled to 0° C., the THF solution (2 ml) of 5'-O-[bis(4-methoxyphenyl)phenylmethyl]uridine (0.5 mmol, 274 mg) and the THF solution (2 ml) of phenyl isocyanate (0.5 mmol, 59.6 mg) are added thereto. After the mixture was continuously stirred for two hours at 0° C., the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 94:6, and the transformation ratio of the reaction was not less than 99%.

$^1$H NMR (400 MHz, CDCl$_3$/ppm): δ3.43 (s, 2H), 3.75 (s, 6H), 4.19 (s, 1H), 4.64-4.65 (m, 1H), 5.32-5.34 (m, 2H), 6.25-6.26 (m, 1H), 6.81-7.39 (m, 18H), 7.70 (d, J=8.3 Hz, 1H), 7.98 (s, 1H), 9.72 (s, 1H)

HPLC Analysis Condition

Column: Lichrospher RP-15, Eluent: acetonitrile/5 mM KH$_2$PO$_4$, K$_2$HPO$_4$ (pH 6.9)=45/55, Flow speed: 1.5 mL/min, Detection wavelength: 254 nm, Column temperature: 40° C., Retention time: 5'-O-[bis(4-methoxyphenyl)phenylmethyl]-2'-O-phenylcarbamoyl-uridine=19.2 min and 5'-O-[bis(4-methoxyphenyl)phenylmethyl]-3'-O-phenylcarbamoyl-uridine=24.1 min Example 2

Production of 5'-O-[bis(4-methoxyphenyl)phenylmethyl]-2'-O-phenylcarbamoyl-uridine The THF solution (1.5 ml) containing 2,6-bis[(4S)-isopropyl-2-oxazoline-2-yl]pyridine (0.03 mmol, 9.1 mg) and copper chloride (II) (0.03 mmol, 4.1 mg) was stirred for one day at room temperature. After the reaction mixture was cooled to −30° C., the THF solution (1.5 ml) of 5'-O-[bis(4-methoxyphenyl)phenylmethyl]uridine (0.3 mmol, 164.3 mg) and the THF solution (1.5 ml) of phenyl isocyanate (0.3 mmol, 35.8 mg) were added thereto. After the mixture was continuously stirred for two hours at −30° C., the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 97:3, and the transformation ratio of the reaction was not less than 99%.

Example 3

Production of 5'-O-[bis(4-methoxyphenyl)phenylmethyl]-2'-O-phenylcarbamoyl-uridine The THF solution (2 ml) containing 2,6-bis[(4S)-isopropyl-2-oxazoline-2-yl]pyridine (0.04 mmol, 12.2 mg) and Cu(OTf)$_2$ (II) (0.04 mmol, 14.8 mg) was stirred for two hours at room temperature. After the reaction mixture was cooled to 0° C., the THF solution of 5'-O-[bis(4-methoxyphenyl)phenylmethyl]uridine (0.4 mmol, 218.6 mg) and the THF solution of phenyl isocyanate (0.4 mmol, 47.7 mg) were added thereto. After the mixture was continuously stirred for 19 hours at 0° C., the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 84:14, and the transformation ratio of the reaction was 76%.

Example 4

Production of 5'-O-[bis(4-methoxyphenyl)phenylmethyl]-2'-O-phenylcarbamoyl-uridine The THF solution (1 ml) containing 2,2'-isopropylidenebis[(4S)-4-tert-butyl-2-oxazoline] (0.03 mmol, 8.9 mg) and Cu(OTf)$_2$ (II) (0.03 mmol, 11.1 mg) was stirred for 2 hours at room temperature. After the reaction mixture was cooled to 0° C., the THF solution (1 ml) of 5'-O-[bis(4-methoxyphenyl)phenylmethyl]uridine (0.3 mmol, 164 mg) and the THF solution of phenyl isocyanate (0.3 mmol, 35.7 mg) were added thereto. After the mixture was continuously stirred at 0° C. overnight, the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 72:28, and the transformation ratio of the reaction was 95%.

Example 5

Production of 5'-O-[bis(4-methoxyphenyl)phenylmethyl]-2'-O-phenylcarbamoyl-uridine The THF solution (1 ml) containing 2,2'-bis[(4S)-4-benzyl-2-oxazoline] (0.02 mmol, 6.5 mg) and Cu(OTf)$_2$ (II) (0.02 mmol, 7.2 mg) was stirred for 2 hours at room temperature. After the reaction mixture was cooled to 0° C., the THF solution (1 ml) of 5'-O-[bis(4-methoxyphenyl)phenylmethyl]uridine (0.2 mmol, 109 mg) and the THF solution (1 ml) of phenyl isocyanate (0.2 mmol, 23.8 mg) were added thereto.

After the mixture was continuously stirred for 1 hour at 0° C. and overnight at room temperature, the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 70:30, and the transformation ratio of the reaction was 83%.

Example 6

Production of 5'-O-[bis(4-methoxyphenyl)phenylmethyl]-2'-O-phenylcarbamoyl-uridine The THF solution (1 ml) containing 2,2'-methylenebis[(4S)-4-tert-butyl-2-oxazoline] (0.02 mmol, 5.4 mg) and Cu(OTf)$_2$ (II) (0.02 mmol, 7.2 mg) was stirred for 2 hours at room temperature. After the reaction mixture was cooled to 0° C., the THF solution (1 ml) of 5'-O-[bis(4-methoxyphenyl)phenylmethyl]uridine (0.2 mmol, 109 mg) and the THF solution (1 ml) of phenyl isocyanate (0.2 mmol, 23.8 mg) were added thereto. After the mixture was continuously stirred for 1 hour at 0° C. and overnight at room temperature, the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 65:35, and the transformation ratio of the reaction was 89%.

Example 7

Production of 5'-O-[bis(4-methoxyphenyl)phenylmethyl]-2'-O-phenylcarbamoyl-uridine The THF solution (1 ml) containing 2,2'-isopropylidenebis[(4S)-4-phenyl-2-oxazoline] (0.02 mmol, 7.2 mg) and Cu(OTf)$_2$ (II) (0.02 mmol, 6.7 mg) was stirred for 30 minutes at room temperature. After the reaction mixture was cooled to 0° C., THF solution (1 ml) of 5'-O-[bis(4-methoxyphenyl)phenylmethyl]uridine (0.2 mmol, 109.3 mg) and THF solution (1 ml) of phenyl isocyanate (0.2 mmol, 23.8 mg) were added thereto. After the mixture was continuously stirred for 1 hour at 0° C. and for 4 hours at room temperature, the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 60:40, and the transformation ratio of the reaction was 96%.

Example 8

Production of 5'-O-[bis(4-methoxyphenyl)phenylmethyl]-2'-O-phenylcarbamoyl-uridine The THF solution (1 ml) containing 2,2'-isopropylidenebis[(4R)-4-phenyl-2-oxazoline] (0.02 mmol, 7.2 mg) and Cu(OTf)$_2$ (II) (0.02 mmol, 6.7 mg) was stirred for 30 minutes at room temperature. After the reaction mixture was cooled to 0° C., the THF solution (1 ml) of 5'-O-[bis(4-methoxyphenyl)phenylmethyl]uridine (0.2 mmol, 109.3 mg) and the THF solution (1.5 ml) of phenyl isocyanate (0.2 mmol, 23.8 mg) were added thereto. After the mixture was continuously stirred for 1 hour at 0° C. and for 1.5 hours at room temperature, the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 50:50, and the transformation ratio of the reaction was 87%.

Example 9

Production of 5'-O-[bis(4-methoxyphenyl)phenylmethyl]-2'-O-phenylcarbamoyl-uridine The THF solution (1 ml) containing 3aR-[2(3'aR,8'aS),3'aβ,8'aβ]]-2,2'-methylenebis[3a,8a-dihydro-8H-indeno-[1,2-d]oxazole] (0.03 mmol, 10.1 mg) and Cu(OTf)$_2$ (II) (0.03 mmol, 11.1 mg) was stirred for 30 minutes at room temperature. After the reaction mixture was cooled to 0° C., the THF solution (1.5 ml) of 5'-O-[bis(4-methoxyphenyl)phenylmethyl]uridine (0.3 mmol, 164.0 mg) and the THF solution (1 ml) of phenyl isocyanate (0.3 mmol, 35.7 mg) were added thereto. After the mixture was continuously stirred for 1 hour at 0° C. and for 1.5 hours at room temperature, the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 82:18, and the transformation ratio of the reaction was 76%.

Example 10

Production of 5'-O-[bis(4-methoxyphenyl)phenylmethyl]-2'-O-phenylcarbamoyl-uridine The THF solution (1 ml) containing 2,6-bis[(4S)-phenyl-2-oxazoline-2-yl]pyridine (0.03 mmol, 11.1 mg) and Cu(OTf)$_2$ (II) (0.03 mmol, 11.1 mg) was stirred for 30 minutes at room temperature. After the reaction mixture was cooled to 0° C., the THF solution (1.5 ml) of 5'-O-[bis(4-methoxyphenyl)phenylmethyl]uridine (0.3 mmol, 164.0 mg) and the THF solution (1 ml) of phenyl isocyanate (0.3 mmol, 35.7 mg) were added thereto. After the mixture was continuously stirred for 19 hours at 0° C., the mixture was analyzed with high-performance liquid chromatography. As a result, it was found that 5'-O-[bis(4-methoxyphenyl)phenylmethyl]-2'-O-phenylcarbamoyl-uridine and 5'-O-[bis(4-methoxyphenyl)phenylmethyl]-3'-O-phenylcarbamoyl-uridine were produced at the ratio of 68:32, and the transformation ratio of the reaction was 81%.

Example 11

Production of 5'-O-[bis(4-methoxyphenyl)phenylmethyl]-2'-O-tert-butyl-carbamoyluridine The THF solution (1.5 ml) containing 2,6-bis[(4S)-isopropyl-2-oxazoline-2-yl]pyridine (0.03 mmol, 9.1 mg) and copper chloride (II) (0.03 mmol, 4.1 mg) was stirred overnight at room temperature. After the reaction mixture was cooled to 0° C., the THF solution (1.5 ml) of 5'-O-[bis(4-methoxyphenyl)phenylmethyl]uridine (0.3 mmol, 176.3 mg) and the THF solution (1.5 ml) of tert-butyl isocyanate (0.3 mmol, 29.7 mg) were added thereto. After the mixture was continuously stirred for 6 hours at 0° C. and for 24 hours at room temperature, the mixture was analyzed with high-performance liquid chromatography. As a result, it was found that 5'-O-[bis(4-methoxyphenyl)phenylmethyl]2'-O-tert-butyl-carbamoyluridine and 5'-O-[bis(4-methoxyphenyl)phenylmethyl]-3'-O- tert-butyl-carbamoyluridine were produced at the ratio of 67:33, and the transformation ratio of the reaction was 90%.

¹H NMR (400 MHz, CDCl₃/ppm): δ1.32 (s, 9H), 3.45-3.52 (m, 2H), 3.79 (s, 6H), 4.12-4.14 (s, 1H), 4.55-4.60 (m, 1H), 5.03-5.04 (m, 1H), 5.16 (t, J=5.3 Hz, 1H), 5.37 (d, J=8.0 Hz, 1H), 6.09 (d, J=4.1 Hz, 1H), 6.81-7.40 (m, 13H), 7.78 (d, J=8.0 Hz, 1H), 8.63-8.72 (m, 1H)

HPLC Analysis Condition

Column: Lichrospher RP-15, Eluent: acetonitrile/5 mM KH₂PO₄, K₂HPO₄ (pH6.9)=60/40, Flow speed: 1.0 mL/min, Detection wavelength: 210 nm, Column temperature: 40° C., Retention time: 5'-O-[bis(4-methoxyphenyl)phenylmethyl]-2'-O-tert-butyl-carbamoyluridine=14.2 min and 5'-O-[bis(4-methoxyphenyl)phenylmethyl]-3'-O-tert-butyl-carbamoyluridine=16.9 min Example 12

Production of 5'-O-[bis(4-methoxyphenyl)phenylmethyl]-N-6-benzoyl-2'-O-phenylcarbamoyladenosine The THF solution (75 ml) containing 2,6-bis[(4S)-isopropyl-2-oxazoline-2-yl]pyridine (0.15 mmol, 45.2 mg) and copper chloride (II) (0.15 mmol, 25.6 mg) was stirred for a day at room temperature. After the reaction mixture was cooled to −15° C., the THF solution (15 ml) of 5'-O-[bis(4-methoxyphenyl)phenylmethyl]-N6-benzoyladenosine (1.5 mmol, 1.0 g) and the THF solution (15 ml) of phenyl isocyanate (1.5 mmol, 178.7 mg) and K₂CO₃ (1.5 mmol, 207.3 mg) were added thereto. After the mixture was continuously stirred for 42 hours at −15° C., the mixture was analyzed with high-performance liquid chromatography. As a result, it was found that 5'-O-[bis(4-methoxyphenyl)phenylmethyl]-N6-benzoyl-2'-O-phenylcarbamoyladenosine and 5'-O-[bis(4-methoxyphenyl)phenylmethyl]-N6-benzoyl-3'-O-phenylcarbamoyladenosine were produced at the ratio of 93:7, and the transformation ratio of the reaction was 99%.

¹H NMR (400 MHz, CDCl₃/ppm): δ3.44-3.56 (m, 2H), 3.77 (s, 6H), 4.30-4.31 (m, 1H), 4.90 (dd, J=4.9 Hz, 1H), 5.88 (dd, J=4.9 Hz, 1H), 6.35 (d, J=5.0 Hz, 1H), 6.80-7.63 (m, 21H), 8.00 (d, J=7.4 Hz, 1H), 8.22 (s, 1H), 8.74 (s, 1H), 8.96 (s, 1H)

HPLC Analysis Condition

Column: Lichrospher RP-15, Eluent: acetonitrile/10 mM aqueous ammonium acetate solution=60/40, Flow speed: 0.5 mL/min, Detection wavelength: 254 nm, Column temperature: 40° C., Retention time: 5'-O-[bis(4-methoxyphenyl)phenylmethyl]-N6-benzoyl-2'-β-phenylcarbamoyladenosine=15.9 min and 5'-O-[bis(4-methoxyphenyl)phenylmethyl]-N6-benzoyl-3'-O-phenylcarbamoyladenosine=18.7 min Example 13

Production of 5'-O-[bis(4-methoxyphenyl)phenylmethyl]-N2-phenoxyacetyl-2'-O-phenylcarbamoylguanosine The THF solution (33 ml) containing 2,6-bis[(4S)-isopropyl-2-oxazoline-2-yl]pyridine (0.06 mmol, 18.1 mg) and copper chloride (II) (0.06 mmol, 10.2 mg) was stirred for a day at room temperature. After the reaction mixture was cooled to −20° C., the THF solution (32 ml) of 5'-O-[bis(4-methoxyphenyl)phenylmethyl]-N2-phenoxyacetyl-guanosine (0.60 mmol, 431.8 mg) and the THF solution (1.6 ml) of phenyl isocyanate (0.60 mmol, 71.5 mg) and K₂CO₃ (0.60 mmol, 82.9 mg) were sequentially added thereto. After the mixture was stirred for 24.5 hours at −20° C., the THF solution (1.6 ml) of phenyl isocyanate (0.60 mmol, 71.5 mg) was added thereto. After the mixture was further stirred for 23.5 hours, the mixture was analyzed with high-performance liquid chromatography. As a result, it was found that 5'-O-[bis(4-methoxyphenyl)phenylmethyl]-N2-phenoxyacetyl-2'-O-phenylcarbamoylguanosine and 5'-O-[bis(4-methoxyphenyl)phenylmethyl]-N2-phenoxyacetyl-3'-O-phenylcarbamoylguanosine were produced at the ratio of 99:1, and the transformation ratio of the reaction was not less than 99%.

¹H NMR (400 MHz, CDCl₃/ppm): δ3.36-3.45 (m, 2H), 3.66 (s, 6H), 4.26-4.31 (m, 1H), 4.38-4.55 (m, 2H), 4.76-4.83 (m, 2H), 5.70-5.80 (m, 1H), 6.15 (d, J=5.6 Hz, 1H), 6.70-7.45 (m, 23H), 7.94 (s, 1H), 9.29 (s, 1H), 11.8 (s, 1H)

HPLC Analysis Condition

Column: NACALAI COSMOSIL 5C8, Eluent: acetonitrile/10 mM aqueous ammonium acetate solution=50/50, Flow speed: 1.0 mL/min, Detection wavelength: 254 nm, Column temperature: 40° C., Retention time: 5'-O-[bis(4-methoxyphenyl)phenylmethyl]-N2-phenoxyacetyl-2'-O-phenylcarbamoylguanosine=26.1 min and 5'-O-[bis(4-methoxyphenyl)phenylmethyl]-N2-phenoxyacetyl-3'-O-phenylcarbamoylguanosine=31.3 min Example 14

Production of 5'-O-[bis(4-methoxyphenyl)phenylmethyl]-N⁴-[bis(4-methoxy-phenyl)phenylmethyl]-2'-O-phenylcarbamoylcytidine The dioxane solution (4 ml) containing 2,6-bis[(4S)-isopropyl-2-oxazoline-2-yl]pyridine (0.02 mmol, 6.2 mg) and Cu(OTf)₂ (II) (0.02 mmol, 7.4 mg) was stirred for 1.25 hours at room temperature. The dioxane solution (1 ml) of 5'-O-[bis(4-methoxyphenyl)phenylmethyl]-N⁴-[bis(4-methoxy-phenyl)phenylmethyl]cytidine (0.2 mmol, 169.6 mg) and the dioxane solution (1 ml) of phenyl isocyanate (0.2 mmol, 23.8 mg) were added thereto. After the mixture was continuously stirred for 4 hours at room temperature, the mixture was analyzed with high-performance liquid chromatography. As a result, it was found that 5'-O-[bis(4-methoxyphenyl)phenylmethyl]-N⁴-[bis(4-methoxy-phenyl)phenylmethyl]-2'-O-phenylcarbamoylcytidine and 5'-O-[bis(4-methoxyphenyl)phenylmethyl]-N⁴-[bis(4-methoxy-phenyl)phenylmethyl]-3'-O-phenylcarbamoylcytidine were produced at the ratio of 85:15, and the transformation ratio of the reaction was 93%.

¹H NMR (400 MHz, CDCl₃/ppm): δ3.42-3.45 (m, 2H), 3.72-3.76 (m, 12H), 4.15-4.20 (m, 1H), 4.50-4.55 (m, 1H), 4.77-4.83 (m, 1H), 5.07-5.12 (m, 1H), 6.30-6.35 (m, 1H), 6.70-7.70 (m, 32H)

HPLC Analysis Condition

Column: YMC Pack ODS-A A303, Eluent: acetonitrile/50 mM aqueous ammonium acetate solution=55/45, Flow speed: 1.0 mL/min, Detection wavelength: 254 nm, Column temperature: 35° C., Retention time: 5'-O-[bis(4-methoxyphenyl)phenylmethyl]-N2-[bis(4-methoxy-phenyl)phenylmethyl]-2'-O-phenylcarbamoylcytidine=22.4 min and 5'-O-[bis(4-methoxyphenyl)phenylmethyl]-N2-[bis(4-methoxyphenyl)phenylmethyl]-3'-O-phenylcarbamoylcytidine=25.9 min Example 15

Production of 5'-O-[bis(4-methoxyphenyl)phenylmethyl]-2'-O-phenylcarbamoyl-uridine 3'-O-(2-cyanoethyl N,N-diisopropylphosphoramidite)

To the stirred methylene chloride solution (2.5 mL) of 5'-O-[bis(4-methoxyphenyl)phenylmethyl]-2'-O-phenylcarbamoyl-uridine (1.0 mmol, 665 mg), the methylene chloride solution (2.5 mL) of bis(N,N-diisopropylamino)cyanoethylphosphite (1.4 mmol, 43 5 mg) and the methylene chloride solution (2.5 mL) of pyridine trifluoroacetate (1.2 mmol, 237 mg) were sequentially added at room temperature. After overnight, methylene chloride was added, and the organic layer was washed with saturated sodium bicarbonate water and brine. The organic layer was dried with anhydrous sodium sulfate, and then concentrated, to obtain a white solid. The solid was crystallized using chloroform and methylcyclohexane. The yield was 97%.

$^1$H NMR (400 MHz, CDCl$_3$/ppm): δ1.05-1.14 (m, 12H), 2.41-2.58 (m, 2H), 3.45-3.70 (m, 6H), 3.79-3.80 (m, 6H), 4.26-4.37 (m, 1H), 4.75-4.85 (m, 1H), 5.30-5.50 (m, 2H), 6.29-6.32 (m, 1H), 6.83-7.73 (m, 19H), 8.45 (s, 1H)

Example 16

Production of 5'-O-[bis(4-methoxyphenyl)phenylmethyl]-2'-O-phenylcarbamoyl-uridine 3'-O-(2-cyanoethyl N,N-diisopropylphosphoramidite)

To the stirred methylene chloride solution (10 mL) of 5'-O-[bis(4-methoxyphenyl)phenylmethyl]-2'-O-phenylcarbamoyl-uridine (2.0 mmol, 1.33 g), diisopropylethylamine (2.87 mmol, 371 mg) and the methylene chloride solution (3.0 mL) of 2-cyanoethyl diisopropylchlorophosphoramidite (2.6 mmol, 615 mg) were sequentially added at room temperature. After the mixture was stirred for 5 hours, methylene chloride was added thereto and washed with saturated sodium bicarbonate water and brine. The organic layer was separated out, and dried with anhydrous magnesium sulfate, and then concentrated, to obtain a white solid. The solid was purified with silica gel column chromatography (hexane:ethyl acetate:pyridine=100:200:6). The yield was 83%.

Example 17

Production of 5'-O-[bis(4-methoxyphenyl)phenylmethyl]-N6-benzoyl-2'-O-phenylcarbamoyl-adenosine 3'-O-(2-cyanoethyl N,N-diisopropylphosphoramidite)

To the stirred methylene chloride solution (2.0 mL) of 5'-O-[bis(4-methoxyphenyl)phenylmethyl]-N6-benzoyl-2'-O-phenylcarbamoyladenosine (0.4 mmol, 317 mg), diisopropylethylamine (0.58 mmol, 75.3 mg) and the methylene chloride solution (1.0 mL) of 2-cyanoethyl diisopropylchlorophosphoramidite (0.44 mmol, 104.1 mg) was sequentially added at room temperature. After 3 hours with stirring, diisopropylethylamine (0.23 mmol, 30.0 mg) and the methylene chloride solution (1.0 mL) of 2-cyanoethyl diisopropylchlorophosphoramidite (0.18 mmol, 41.7 mg) were further added. After 1.5 hours with stirring, methylene chloride was added thereto and the organic layer was washed with a saturated sodium bicarbonate water and brine. The organic layer was separated out, and dried with anhydrous sodium sulfate, and concentrated to obtain a white solid. The solid was analyzed with high-performance liquid chromatography; as a result, it was found that the transformation ratio of the reaction was not less than 99%.

$^1$H NMR (400 MHz, CDCl$_3$/ppm): δ1.06-1.18 (m, 12H), 2.38-2.70 (m, 2H), 3.40-3.70 (m, 6H), 3.76-3.77 (m, 6H), 4.39-4.51 (m, 1H), 4.95-5.08 (m, 1H), 5.89-6.08 (m, 1H), 6.36-6.43 (m, 1H), 6.78-8.08 (m, 23H), 8.23 (s, 1H), 8.74-8.80 (m, 1H), 9.04 (s, 1H)

HPLC Analysis Condition

Column: NACALAI COSMOSIL 5C8, Eluent: acetonitrile/10 mM aqueous ammonium acetate solution (pH 6.9)=70/30, Flow rate: 0.5 mL/min, Detection wavelength: 254 nm, Column temperature: 40° C., Retention time: 5'-O-[bis(4-methoxyphenyl)phenylmethyl]-N6-benzoyl-2'-O-phenylcarbamoyl-adenosine 3'-O-(2-cyanoethyl N,N-diisopropylphosphoramidite)=24.4, 27.2 min Example 18

Production of 5'-O-[bis(4-methoxyphenyl)phenylmethyl]-N2-phenoxyacetyl-2'-O-phenylcarbamoylguanosine 3'-O— (2-cyanoethyl N,N-diisopropylphosphoramidite)

To the stirred methylene chloride solution (12 mL) of 5'-O-[bis(4-methoxyphenyl)phenylmethyl]-N2-phenoxyacetyl-2'-O-phenylcarbamoylguanosine (2.3 mmol, 1.95 g), diisopropylethylamine (3.4 mmol, 437 mg) and the methylene chloride solution (2.0 mL) of 2-cyanoethyl diisopropylchlorophosphoramidite (2.6 mmol, 622 mg) was sequently added at room temperature. After 21 hours with stirring, the methylene chloride solution (0.6 mL) of 2-cyanoethyl diisopropylchlorophosphoramidite (0.2 mmol, 60 mg) was further added. After 3 hours, diisopropylethylamine (1.0 mmol, 131 mg) and the methylene chloride solution (0.6 mL) of 2-cyanoethyl diisopropylchlorophosphoramidite (0.5 mmol, 127 mg) was further added. The mixture was stirred for 1.5 hours at room temperature, and then, methylene chloride was added thereto and the organic layer was washed with saturated sodium bicarbonate water and brine. The organic layer was separated out, and dried with anhydrous sodium sulfate, and concentrated to obtain a white solid. The solid was analyzed with high-performance liquid chromatography; as a result, it was found that the transformation ratio of the reaction was 90%. The solid was purified with silica gel column chromatography (acetone:hexane:pyridine=100:150:5); as a result, the yield was 57%.

$^1$H NMR (400 MHz, CDCl$_3$/ppm): δ1.03-1.18 (m, 12H), 2.35-2.69 (m, 2H), 3.35-3.70 (m, 6H), 3.76 (s, 6H), 4.32-4.49 (m, 1H), 4.51-4.56 (m, 2H), 4.81-4.88 (m, 1H), 5.82-5.95 (m, 1H), 6.10-6.21 (m, 1H), 6.75-6.82 (m, 4H), 6.90-7.45 (m, 19H), 7.86 (s, 1H)

HPLC Analysis Condition

Column: NACALAI COSMOSIL 5C8, Eluent: acetonitrile/10 mM aqueous ammonium acetate solution=70/30, Flow rate: 0.5 mL/min, Detection wavelength: 254 nm, Column temperature: 40° C., Retention time: 5'-O-[bis(4-methoxyphenyl)phenylmethyl]-N2-phenoxyacetyl-2'-O-phenylcarbamoyl-guanosine 3'-O-(2-cyanoethyl N,N-diisopropylphosphoramidite)=25.3, 28.3 min Example 19

Production of 5'-O-[bis(4-methoxyphenyl)phenylmethyl]-2'-O-phenylcarbamoylcytidine 3'-O-(2-cyanoethyl N,N-diisopropylphosphoramidite)

To the acetonitrile solution of 5'-O-[bis(4-methoxyphenyl) phenylmethyl]-2'-O-phenylcarbamoyl-uridine 3'-O-(2-cyanoethyl N,N-diisopropylphosphoramidite) (0.88 mmol, 765.5 mg) and POCl$_3$ (1.88 mmol, 287.5 mg) and triethylamine (21.6 mmol, 2.186 g), 1,2,4-triazole (20.7 mmol, 1.459 g) was added dropwise at room temperature. The mixture was stirred for 2 hours. Ethyl acetate (150 ml) was added thereto, and the organic layer was washed with a 5% $Na_2CO_3$ aqueous solution twice and distilled water once. The organic layer was dried with anhydrous sodium sulfate, and concentrated to obtain a pale yellow solid. The solid was dissolved in a mixed solvent of pyridine and ammonia, and the solution was stirred for 2.8 hours at room temperature. The solvent was distilled away, and the residue was subject to azeotropy with toluene and purified with silica gel column chromatography. The isolated yield was 93%.

$^1$H NMR (400 MHz, $CDCl_3$/ppm): δ0.98-1.11 (m, 12H), 2.31-2.45 (m, 2H), 3.42-3.75 (m, 6H), 3.79 (s, 3H), 3.80 (s, 3H), 4.25-4.37 (m, 1H), 4.75-4.82 (m, 1H), 5.20-5.48 (m, 2H), 6.49-6.52 (m, 1H), 6.84-7.50 (m, 18H), 7.87-7.91 (m, 1H)

HPLC Analysis Condition

Column: Mightysil manufactured by KANTO KAGAKU, Eluent: acetonitrile/10 mM aqueous ammonium acetate solution=60/40→90/10, Flow rate: 0.5 mL/min, Detection wavelength: 254 nm, Column temperature: 40° C., Retention time: 5'-O-[bis(4-methoxyphenyl)phenylmethyl]-2'-O-phenylcarbamoyl-cytidine 3'-O-(2-cyanoethyl N,N-diisopropylphosphoramidite)= 26.5, 28.3 min Comparative Example Production of 5'-benzoyl-N6-benzyl-2'-O-phenylcarbamoyladenosine The toluene-DMF mixed solvent solution of 5'-benzoyl-N6-benzyladenosine (0.1 mmol) and bis(tributyltin) oxide (0.05 mmol) and phenyl isocyanate (0.2 mmol) was stirred at −78° C. to −48° C. for 49 hours, to obtain 5'-benzoyl-N6-benzyl-2'-O-phenylcarbamoyladenosine with the yield of 60% and 5'-benzoyl-N6-benzyl-3'-O-phenylcarbamoyladenosine with the yield of 40%.

The invention claimed is:

1. A method for producing a 2'-hydroxy-protected ribonucleoside derivative, wherein the 2'-hydroxy-protected ribonucleoside derivative is represented by the formula (2):

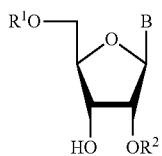

(2)

wherein, $R^1$ is a hydrogen atom or a protective group for a hydroxy group; $R^2$ is an acyl or a carbamoyl group; B is 9-adeninyl, 9-guaninyl, 1-cytosinyl, 1-uracilyl or a protected derivative thereof, represented by the following formula:

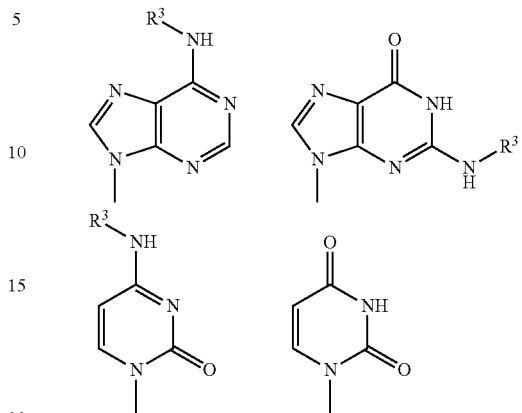

wherein, $R^3$ is a hydrogen atom or a protective group for an amino group;

comprising a step of reacting a ribonucleoside represented by the formula (1):

(1)

wherein, $R^1$ and B mean the same as the above, with an acylating or a carbamoylating reagent in the presence of a copper complex consisting of a copper compound and an optically active ligand, to regioselectively introduce an acyl or a carbamoyl group in place of the 2'-hydroxy group.

2. The production method according to claim 1, wherein the copper compound is represented by the formula (3):

$$CuX_2 \qquad (3)$$

wherein, X is a halogen atom, OTf, $ClO_4$, $BF_4$, $SbF_6$ or $PF_6$.

3. The production method according to claim 2, wherein X is Cl or OTf.

4. The production method according to claim 1, wherein the optically active ligand is an optically active imine ligand.

5. The production method according to claim 4, wherein the optically active imine ligand is represented by the formula (10):

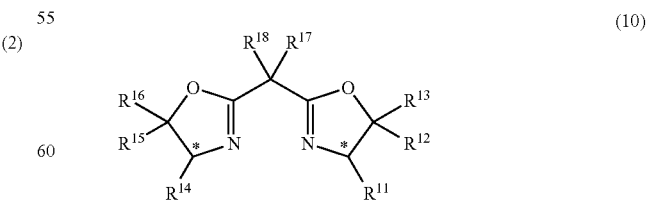

(10)

wherein, $R^{11}$ and $R^{14}$ are independently an optionally substituted alkyl group, an optionally substituted alkenyl group, an optionally substituted alkynyl group, an optionally substituted cycloalkyl group, an optionally substituted aralkyl group or an optionally substituted aryl group; $R^{12}$, $R^{15}$, $R^{13}$ and $R^{16}$ are independently a hydrogen atom, an optionally substituted alkyl group, an optionally substituted alkenyl group, an optionally substituted alkynyl group, an optionally substituted cycloalkyl group, an optionally substituted aralkyl group or an optionally substituted aryl group; $R^{11}$ may be bound to $R^{12}$ or $R^{13}$ and $R^{14}$ may be bound to $R^{15}$ or $R^{16}$, to form a ring; $R^{17}$ and $R^{18}$ may be the same or different each other, and is a hydrogen atom, an alkyl group or a cycloalkyl group; and * indicates an asymmetric carbon; or the formula (11):

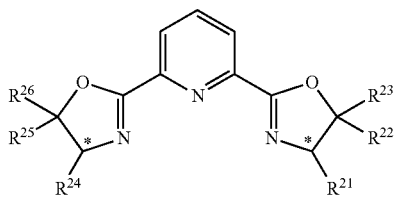

(11)

wherein, $R^{21}$ and $R^{24}$ are independently an optionally substituted alkyl group, an optionally substituted alkenyl group, an optionally substituted alkynyl group, an optionally substituted cycloalkyl group, an optionally substituted aralkyl group or an optionally substituted aryl group; $R^{22}$, $R^{25}$, $R^{23}$ and $R^{26}$ are independently a hydrogen atom, an optionally substituted alkyl group, an optionally substituted alkenyl group, an optionally substituted alkynyl group, an optionally substituted cycloalkyl group, an optionally substituted aralkyl group or an optionally substituted aryl group; $R^{21}$ may be bound to $R^{22}$ or $R^{23}$ and $R^{24}$ may be bound to $R^{25}$ or $R^{26}$, to form a ring; and * indicates an asymmetric carbon.

6. The production method according to claim 5, wherein $R^{22}$, $R^{23}$, $R^{25}$ and $R^{26}$ are hydrogen atoms and $R^{21}$ and $R^{24}$ are isopropyl groups.

7. The production method according to claim 1, wherein the carbamoylating reagent is represented by the formula (4):

$$R^4NCO \quad (4)$$

wherein, $R^4$ is an optionally substituted alkyl group having 1 to 18 carbon atoms, an optionally substituted cycloalkyl group having 1 to 18 carbon atoms, an optionally substituted aryl group having 6 to 18 carbon atoms, an optionally substituted aralkyl group having 7 to 18 carbon atoms, an optionally substituted sulfonyl group or an optionally substituted silyl group.

8. The production method according to claim 7, wherein $R^4$ is an optionally substituted phenyl group.

9. The production method according to claim 1, further comprising wherein the reaction is carried out in the presence of a base.

10. The production method according to claim 9, wherein the base is triethylamine, diisopropylethylamine, or potassium carbonate.

11. The production method according to claim 1, wherein tetrahydrofuran and/or dioxane is provided as a reaction solvent.

12. A 5'-O-[bis(4-methoxyphenyl)phenylmethyl]-2'-O-arylcarbamoylnucleoside derivative, represented by the formula (5):

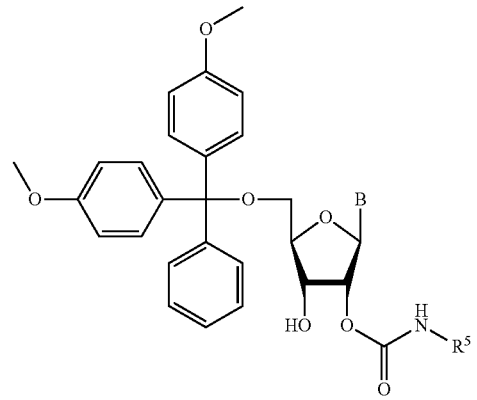

(5)

wherein, B is 9-adeninyl, 9-guaninyl, 1-cytosinyl, 1-uracilyl or a protected derivative thereof, represented by the following formula:

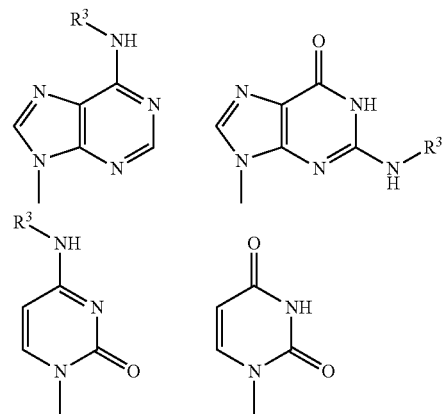

wherein, $R^3$ is a hydrogen atom or a protective group for an amino group;

and $R^5$ is an optionally substituted aryl group having 6 to 18 carbon atoms.

13. The derivative according to claim 12, wherein $R^5$ is a phenyl group.

14. A 5'-O-[bis(4-methoxyphenyl)phenylmethyl]-2'-O-arylcarbamoylribonucleotide 3'-(2-cyanoethyl diisopropylphosphoroamidite) derivative represented by the formula (6):

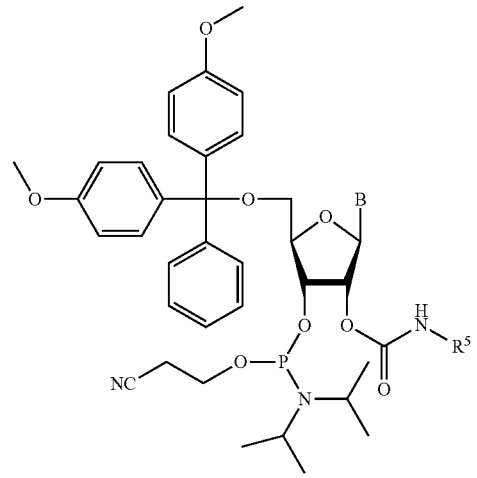

(6)

wherein, B is 9-adeninyl, 9-guaninyl, 1-cytosinyl, 1-uracilyl or a protected derivative thereof, represented by the following formula:

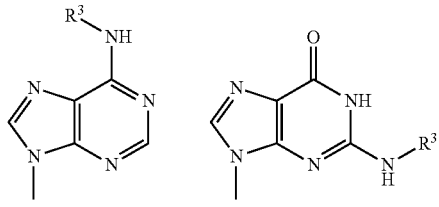

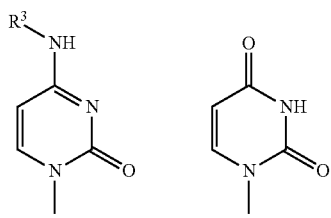

wherein, R³ is a hydrogen atom or a protective group for an amino group;

and R⁵ is an optionally substituted aryl group having 6 to 18 carbon atoms.

15. The derivative according to claim 14, wherein R⁵ is a phenyl group.

16. A method for producing a 2'-protected nucleoside derivative, comprising a step of aminating the oxo group at 4-position of 1-uracilyl in the compound represented by the formula (6) according to claim 14 wherein B is 1-uracilyl, and optionally protecting the amino group, to obtain an optionally amino-protected cytidine derivative.

17. A method for producing a 5'-O-[bis(4-methoxyphenyl) phenylmethyl]-2'-O-arylcarbamoylribonucleotide 3'-(2-cyanoethyl diisopropylphosphoroamidite) derivative represented by the formula (6):

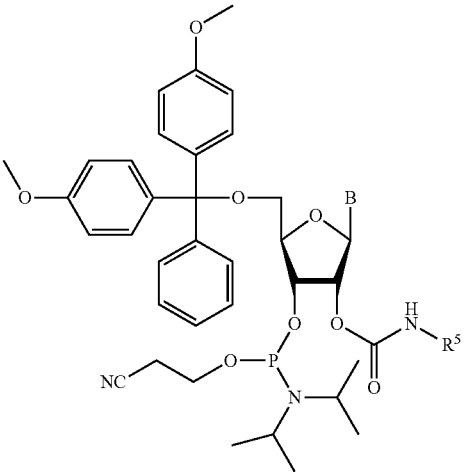

wherein, B is 9-adeninyl, 9-guaninyl, 1-cytosinyl, 1-uracilyl or a protected derivative thereof, represented by the following formula:

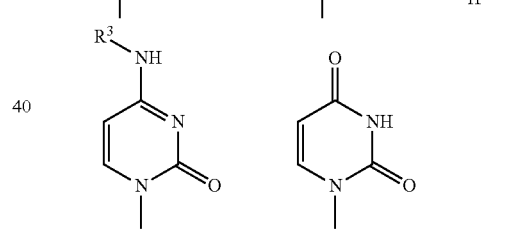

wherein, R³ is a hydrogen atom or a protective group for an amino group;
and R⁵ is an optionally substituted aryl group having 6 to 18 carbon atoms,
comprising a step of phosphitylating the 5'-O-[bis(4-methoxyphenyl)phenylmethyl]-2'-O-arylcarbamoylnucleoside derivative represented by the formula (5) according to claim 12.

18. The production method according to claim 17, wherein R⁵ is a phenyl group.

* * * * *